United States Patent [19]

Flower et al.

[11] 4,405,044

[45] Sep. 20, 1983

[54] DISPENSER BOX FOR PACKAGES OF STERILE SUTURES

[75] Inventors: David I. Flower, Bridgewater; Michael Schuler, Edison, both of N.J.

[73] Assignee: Ethicon, Inc., Somerville, N.J.

[21] Appl. No.: 303,283

[22] Filed: Sep. 17, 1981

[51] Int. Cl.³ .................... B65D 83/08; B65D 5/72
[52] U.S. Cl. ......................... 206/44.12; 206/45.31; 229/17 B
[58] Field of Search ............ 206/44.12, 499, 459, 206/45.31, 45.33, 494; 229/17 B

[56] References Cited

U.S. PATENT DOCUMENTS

| 2,755,922 | 7/1956 | Volckening | 206/45.33 |
| 2,767,832 | 10/1956 | Silberman | 206/45.33 |
| 3,014,634 | 12/1961 | Humphrey et al. | 229/17 B |
| 3,580,472 | 5/1971 | Stawski | 206/499 |
| 3,586,206 | 6/1971 | Gilmore et al. | 206/499 |

Primary Examiner—William T. Dixson, Jr.
Attorney, Agent, or Firm—Robert L. Minier

[57] ABSTRACT

A dispenser for packages of sterile suture materials. The dispenser will dispense either single packages or a plurality of packages. The dispenser has means for determining the quantity of sutures remaining in the dispenser.

8 Claims, 3 Drawing Figures

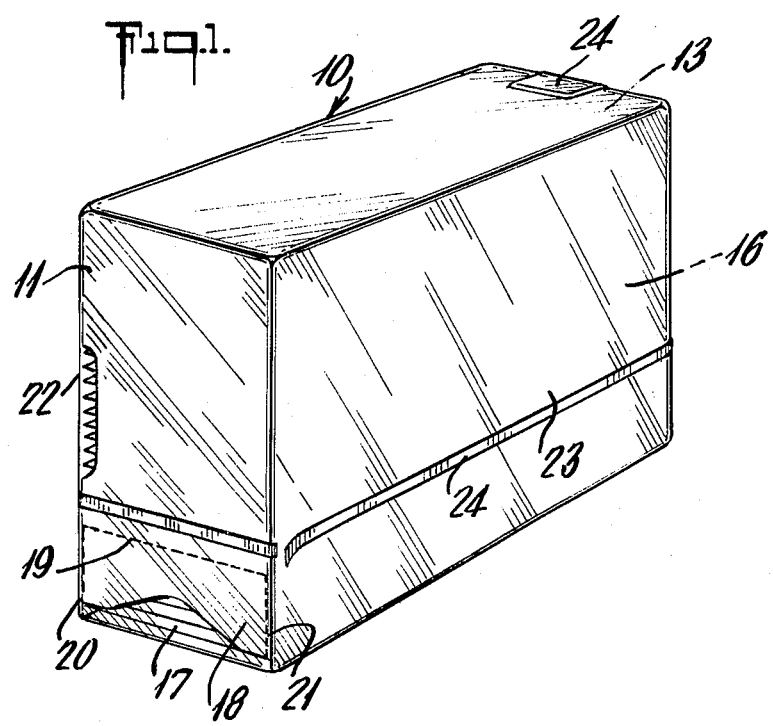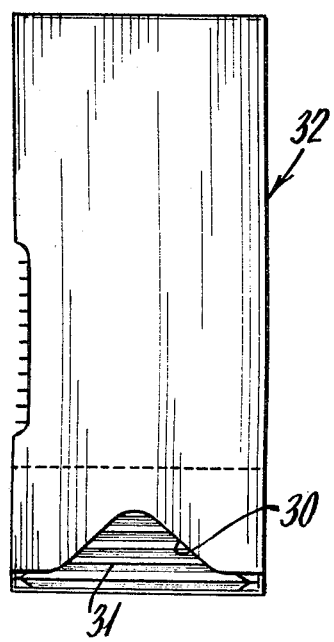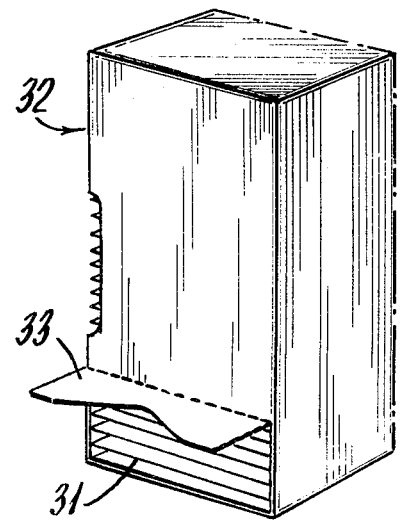

DISPENSER BOX FOR PACKAGES OF STERILE SUTURES

The present invention relates to an improved dispenser box and more particularly to a new and improved dispenser box for packages of sterile suture materials and related surgical items.

BACKGROUND OF THE INVENTION

The suture materials are generally packaged in a sterile manner in foil or a combination of foil and film or foil and paper packages. The sutures are usually packaged either as a single suture in a package or as a plurality of sutures in a package and they may be packaged with needles attached or without needles. Dispensers for such suture materials or similar packages of various types are well known in the art. Patents which are representative of various types of dispensers both for suture packages and other materials are described in U.S. Pat. Nos. 4,004,691; 4,030,596; 4,138,052; 4,197,985 and 4,252,236.

A dispenser box will carry a specific size and style or type of suture. A plurality of the dispenser boxes, each carrying a different size and type of suture, are maintained together in a suitable rack for easy access to virtually all the types and sizes of sutures that may be required in a specific surgical procedure.

In providing for the dispensing of packages of sterile suture materials, a number of things need to be considered and are desirable. The dispenser should be such that it is readily apparent to the user the type of suture material contained in the dispenser. The packages should be readily accessible so that either the nurse or the surgeon when obtaining the suture can do so with the utmost of ease. Furthermore, the package or the dispenser should be such that either single packages or a plurality of packages may be removed from the dispenser at one time. The dispenser should be such that it provides a means of verifying that it contains a sufficient quantity of required suture packages prior to the start of a surgical procedure. Furthermore, the dispenser should be constructed or contained in such a way as to minimize the amount of dust or airborne contaminants that may enter the dispenser and accumulate on the suture packages.

SUMMARY OF THE PRESENT INVENTION

Our new and improved dispenser provides easy and simple access either to a single package of sutures or to a plurality of packages of sutures. Furthermore, our new dispenser allows for ready determination of the inventory or the amount of suture packages remaining in the dispenser. In one embodiment of our present invention, our new dispenser is color coded to allow the user to easily determine the suture materials in the dispenser. In another embodiment of the present invention, our dispenser is covered over its major area by a suitable dust protector to assist in maintaining the entire dispenser clean.

The improved dispenser for packages of sterile surgical suture materials of the present invention comprises a front and rear panel, a top and bottom panel and a pair of side panels. An opening is disposed at the bottom of the front panel abutting the bottom panel for removing a single package of suture material from said dispenser. An area of the front panel adjacent the opening is easily deflectable. In a preferred embodiment of the present invention the deflectable portion of the front is bounded by a scored or perforated line extending transverse of the front panel and spaced from the opening, and a pair of lines extending from the scored line to the opening and spaced where the front panel abuts the side panels. This provides for easily deflectable area adjacent the opening for removal of a plurality of packages of sterile suture materials at one time. A viewing means is disposed in the front panel. In a preferred embodiment the viewing means is an opening disposed vertically in the front panel and extending at least one-fifth the distance between the top and bottom panels to allow for ready determination of the amount of packages of suture materials remaining in the dispenser. In certain embodiments of the dispenser of the present invention, the contents of the dispenser are color coded in a manner so that the color can be seen through one or more of the openings in the front panel for easy determination of the type of suture materials in the dispenser. In another embodiment of the dispenser of the present invention, the entire package is encased in clear plastic material, such as cellophane, with a suitable tear strip about the circumference of the dispenser immediately adjacent the deflectable area of the front panel. In use the tear strip may be removed, the bottom portion of the film wrapper removed leaving the upper portion of the film wrapper on the dispenser to assist in maintaining the dispenser dust free during use. The invention will be more fully described in conjunction with the accompanying drawing. In yet other embodiments of the dispenser of the present invention, the dispenser will include means to removably secure the dispenser to a suitable rack holding a plurlity of dispensers. The securement of the dispenser to a rack allows for packages of sutures to be removed from the dispenser single-handedly. One means for removably securing a dispenser within a rack is to provide one or more of the panels of the dispenser with raised or recessed areas or tabs which will frictionally engage either the surface of adjacent dispensers or a portion of the rack itself.

BRIEF DESCRIPTION OF THE DRAWINGS

FIG. 1 is a perspective view of the improved dispenser of the present invention with a film dust cover about the entire dispenser;

FIG. 2 is a front view of a dispenser of the present invention with the dust cover removed; and FIG. 3 is a partial perspective view of the dispenser of the present invention showing the deflectable area of the front panel.

DETAILED DESCRIPTION OF THE PREFERRED EMBODIMENTS

Referring to the drawings, in FIG. 1 there is shown an improved dispenser 10 of the present invention. The dispenser comprises a front panel 11, a corresponding rear panel, a top panel 13, and a corresponding bottom panel and a pair of side panels 16. An opening 17 is disposed at the bottom of the front panel abutting the bottom panel. Adjacent this opening is deflectable area 18. In this embodiment, the deflectable area is attached to the remainder of the front panel by a scored line 19. In other embodiments a perforated line could be provided to allow for deflectability in the area. The lines 20 and 21 where the deflectable section abuts the side panels are perforated, or in some instances, could even be fully severed, to allow for easy deflectability of this area 18. An opening 22 is disposed along the left-hand edge where the front panel 11 and a side panel meet. Preferably, this opening extends downward from the mid-point of the distance between the top panel 13 and the bottom panel so that viewing of the relative amount of packages remaining in the dispenser is obtained. In certain embodiments, the opening 22 may extend around the edge and include part of the side panel to further improve the viewing. The entire package is enclosed in a transparent film 23 such as cellophane to keep it clean during transportation, storage, etc. When the package is to be used, the tear strip 24 may be removed and the bottom portion of the film wrap discarded. The top portion of the film may either be removed or be allowed to remain on the dispenser to assist in maintaining the dispenser dust free.

At the rear portion of the top panel there is placed a raise area 24. This area is disposed so as to engage a portion of a rack holding a plurality of dispensers. The raised area frictionally engages the rack to removably secure the dispenser to the rack and allow for suture packages to be removed from opening 17 with one hand. The raised area may also be a recessed area or a tab or flap and may be disposed on either the top or bottom panels or side panels as desired.

As seen FIG. 2, in use, it is a simple matter for the individual desiring to take a suture package from the dispenser to insert his fingers in the opening 30 and remove a single package of the suture material 31 from the dispenser 32. As is more clearly shown in FIG. 3, if it is desired that a plurality of suture material be obtained at one time, it is a simple matter for the individual desiring the sutures to deflect the deflectable portion 33 of the front panel and remove the desired packages of sutures from the dispenser.

In the preferred embodiments of the present invention, the outside of the dispenser box is partially color coded; that is, it is colored such that it corresponds to a specific type and/or size of suture so that these colors assist the user in easily obtaining the type of suture he is seeking. Also, a part of the outer portions of the package are preferably white to improve visability of product codes and other pertinent product information. These dispensers are preferably made from paperboard materials such as solid bleached sulfate board. These materials such as solid bleached sulfate board. These materials are easily formed and folded and can be readily perforated or scored and also are suitable for printing. Dust covers may be made from any suitable transparent film. Suture packages, though they form no part of the present invention, are usually foil wrapped packages of either a single suture or a plurality of sutures. They are generally rectangular in shape and relatively thin and a dispenser will contain anywhere from two to fifty or more packages.

Having now described the present invention, it will be readily apparent to those skilled in the art that many variations and modifications may be made without departing from the spirit and scope of the invention.

What is claimed is:

1. A dispenser for a plurality of packages of sterile suture materials comprising a front panel and a rear panel, a top panel and a bottom panel, and a pair of side panels, an opening disposed at the bottom of the front panel and abutting the bottom panel for removing a single suture package from said dispenser, an area of said front panel adjacent said opening panel being easily deflectable to allow for removal of a plurality of suture packages at one time and viewing means disposed vertically in the front panel to allow for ready determination of the amount of packages of sutures remaining in said dispenser.

2. A dispenser for a plurality of packages of sterile suture materials, said dispenser comprising a front panel and a rear panel, a top panel and a bottom panel, and a pair of side panels, an opening disposed at the bottom of the front panel and abutting the bottom panel for removing a single suture package from said dispenser, an area of said front panel adjacent said opening, said area being easily deflectable to allow for removal of a plurality of suture packages at one time, said deflectable are being bounded by a scored line extending transverse of the front panel and a pair of weakened or severed areas connecting the front panel to the side panels and extending from the scored line to the opening, viewing means disposed vertically in the front panel to allow for ready determination of the amount of packages remaining in said dispenser, said viewing means extending at least one-fifth of the distance between the top panel and the bottom panel and said dispenser being encased in an easily removable transparent cover.

3. A dispenser according to claim 2 wherein the viewing opening is disposed adjacent one edge where the front panel meets the side panel and said opening extends into the side panel.

4. A dispenser according to claim 2 wherein the cover may be removed only in part.

5. A dispenser according to claim 1, 3, or 4 wherein the deflectable area adjacent said opening is bounded by a scored line extending transverse of the front panel and a pair of weakened or severed areas connecting the front panel to the side panels and extending from the scored line to the opening.

6. A dispenser according to claim 1, 3 or 4 wherein the deflectable area comprises an area adjacent the openings, said being unconnected to the side panels but being connected to the front panel by a scored line.

7. A dispenser according to claim 2 including means for removably securing said dispenser to a holding rack for a plurality of dispensers whereby suture packages may be removed from said dispenser with one hand.

8. A dispenser according to claim 7 wherein the means for removably securing said dispenser is a raised area disposed in the top, bottom or side panels of the dispenser.

* * * * *